(12) United States Patent (10) Patent No.: US 7,097,832 B1
Kornowski et al. (45) Date of Patent: Aug. 29, 2006

(54) INTRAMYOCARDIAL INJECTION OF AUTOLOGOUS BONE MARROW

(75) Inventors: Ran Kornowski, Ramat hasharon, IL (US); Shmuel Fuchs, Rockville, MD (US); Stephen E. Epstein, Rockville, MD (US); Martin B. Leon, New York, NY (US)

(73) Assignee: Myocardial Therapeutics, Inc., San Diego, CA (US)

( * ) Notice: Subject to any disclaimer, the term of this patent is extended or adjusted under 35 U.S.C. 154(b) by 0 days.

(21) Appl. No.: 09/868,411

(22) PCT Filed: Mar. 30, 2000

(86) PCT No.: PCT/US00/08353

§ 371 (c)(1),
(2), (4) Date: Jun. 14, 2001

(87) PCT Pub. No.: WO00/57922

PCT Pub. Date: Oct. 5, 2000

Related U.S. Application Data

(60) Provisional application No. 60/126,800, filed on Mar. 30, 1999, provisional application No. 60/138,379, filed on Jun. 9, 1999.

(51) Int. Cl.
*A01N 63/00* (2006.01)
*C12N 5/00* (2006.01)
*C12N 5/06* (2006.01)

(52) U.S. Cl. ........................ 424/93.7; 435/384; 435/372

(58) Field of Classification Search ................ 424/94.1, 424/577; 514/2, 21; 435/325
See application file for complete search history.

(56) References Cited

U.S. PATENT DOCUMENTS 5,610,056 A * 3/1997 Nakahata .................... 435/378
5,817,773 A    10/1998 Wilson et al.
5,980,893 A * 11/1999 Avraham et al. ........... 424/144.1
5,997,860 A * 12/1999 Bauer et al. ............... 424/93.71
6,013,780 A     1/2000 Neufeld et al.
6,676,937 B1 * 1/2004 Isner et al. ................. 424/93.7
2005/0031600 A1* 2/2005 Mickle et al. .............. 424/93.7

FOREIGN PATENT DOCUMENTS

WO    WO 91/04274    4/1991
WO    WO 99/00486    1/1999
WO    WO00/57922     10/2000

OTHER PUBLICATIONS

Perin et al. Circulation, 2003; 107 :2294-2302.*
Stamm et al. Lancet, 2003 ; 361 :45-6.*
Tao and Ma. Pathology, 2003; 35:6-13.*
Tomita et al. Circulation, 1999 ; 100(Supp II) :II-247-II-256.*
Chiu, RC. Expert. Opin. Biol. Ther. 2003; 3(2):215-25.*
Liechty et al. Nat. Med. 2000; 6(11): 1282-1286.*
Aoki et al. Blood. Jun. 1999; 93:4034-43.*
Mack et al. J. Thor. Cardio. Surg. 1998; 115:168-77.*
Cashman et al. Blood, 1998; 92: 2338-44.*
Fuchs et al. J. Am. Coll. Cardiol. 2001; 37: 1726-32.*
S. Fuchs, et al., "Transendocardial Delivery of Autologous Bone Marrow Enhances Collateral Perfusion and Regional Function in Pigs with Chronic Experimental Myocardial Ischemia," *Journal of American College of Cardiology*, 2001, vol. 37, No. 6, pp. 1726-1732.
C. Kalka, et al., "Angiogenesis and Vasculogenesis," *Herz*, 2000, vol. 25, No. 6, pp. 611-622.
B.E. Strauer, M.D., et al., "Stem Cell Therapy in Perspective," *Circulation*, 2003, vol. 107, pp. 929-934.
Blume and Thomas, "A Review of Autologous Hematopoietic Cell Transplantation," *Biology of Blood and Marrow Transplantation*, vol. 6, 2000, pp. 1-12.
Brugger, Wolfram et al., "Ex Vivo Manipulation of Hematopoietic Stem and Progenitor Cells," *Seminars in Hematology*, vol. 37, No. 1, Supplement 2, Jan. 2000, pp. 42-49.
Dini, G. et al., "Peripheral Blood Stem Cell Collection from G-CSF-Stimulated Unrelated Donors for Second Transplant," *Bone Marrow Transplantation*, vol. 22, Supplement 5, 1998, pp. S41-S45.
Fielding and Goldstone, "Autologous Bone Marrow Transplantation," *Current Opinion in Hematology*, vol. 1, 1994, pp. 412-417.
Kanj, Souha S. et al., "Myocardial Ischemia Associated With High-Dose Carmustine Infusion," *Cancer*, vol. 68, Nov. 1, 1991, pp. 1910-1912.
Noishiki, Yasuharu et al., "Angiogenic Growth Factor Release System for In Vivo Tissue Engineering: A Trial of Bone Marrow Transplantation into Ischemic Myocardium," *J. Artif. Organs*, vol. 2, 1999, pp. 85-91.
Simnett, S.J. et al., "Autologous Stem Cell Transplantation for Malignancy: A Systematic Review of the Literature," *Clin. Lab. Haem.*, vol. 22, 2000, pp. 61-72.
Vaughan, William P., et al., "Roundtable Discussion: Incorporating Bone Marow Transplantation Into NCCN Guidelines," *Onocology*, vol. 12, No. 11A, NCCN Proceedings, Nov. 1998, pp. 390-392.

(Continued)

*Primary Examiner*—Nancy Vogel
(74) *Attorney, Agent, or Firm*—DLA Piper Rudnick Gray Cary US LLP

(57) ABSTRACT

A method of treating cardiac or myocardial conditions comprises the administration of an effective amount of autologous bone marrow. The bone marrow may optionally be stimulated and/or administered in combination with a pharmaceutical drug, protein, gene or other factor or therapy that may enhance bone marrow production of angiogenic growth factors and/or promote endothelial cell proliferation or migration or blood vessel formation.

15 Claims, 2 Drawing Sheets

OTHER PUBLICATIONS

Dubrey et al., "Improvement of Echocardiographic and Electrocardiographic features in AL Cardiac Amyloidosis with Intensive Melphalan and Autologous Stem Cell Rescue" *Boston University School of Medicine*, XP-00107 135.

Isner and Asahara, "Angiogenesis and vasculogenesis as therapeutic strategies for postnatal neovascularization" *The Journal of Clinical Investigation* 103 (9):1231-1236 (1999).

Karen K. Fields, "Autologous Bone Marrow Transplantation and Melanoma: A Focused Review of the Literature" *Annals of Plastic Surgery* 28 (1):70-73 (1992), XP-001069809.

Noishiki et al., "Autocrine angiogenic vascular prosthesis with bone marrow transplantation" *Nature Medicine*, 2 (1):90-93 (1996).

Tomita et al., "Autotransplanted Mesenchymal Stem Cells Improve Functions After A Myocardial Infarction," *Circulation* 98 (17):1200 Abstract 1037.

Yamauchi et al., "New agents for the treatment of infracted myocardium" *The FASEB Journal* 10.1096/fj.99-0565fje (2000).

S. Fuchs, et al., "Transendocardial Delivery of Autologous Bone Marrow Enhances Collateral Perfusion and Regional Function in Pigs with Chronic Experimental Myocardial Ischemia," *Journal of American College of Cardiology*, 2001, vol. 37, No. 6, pp. 1726-1732.

C. Kalka, et al., "Angiogenesis and Vasculogenesis," *Herz*, 2000, vol. 25, No. 6, pp. 611-622.

B.E. Strauer, M.D., et al., "Stem Cell Therapy in Perspective," *Circulation*, 2003, vol. 107, pp. 929-934.

Anderson, "Human gene therapy", *Nature*, 392(6679 Supp.):25-30 (Apr. 1998).

Bickenbach et al., "Selection and Extended Growth of Murine Epidermal Stem Cells in Culture", *Exp. Cell Res.*, 244(1):184-195 (Oct. 1998).

Blanquaert et al., "RGTA modulates the healing pattern of a defect in a monolayer of osteoblastic cells by acting on both proliferation and migration", *J. Biomed. Mater. Res.*, 64A(3):525-532 (Mar. 2003).

Asahara, T. et al., "Gene therapy of endothelial progenitor cell for vascular development in severe ischemic disease", *Circulation*, vol. 100, (1999) pp. 1-481, Abstract XP009051610.

Isner, Jeffrey M., "Myocardial gene Theapy", *Nature* (London) vol. 415, No. 6868, (2002) pp. 234-239.

Chiu, "Adult stem cell therapy for heart failure", *Expert Opin Biol Ther.*, Apr. 2003, 3(2):215-25.

Desgranges et al., "Beneficial use of fibroblast growth factor 2 and RGTA, a new family of heparan mimics, for endothelialization of PET prostheses", *J Biomed Mater Res.*, 2001, 58(1):1-9.

Dowell et al., "Myocyte and myogenic stem cell transplantation in the heart", *Cardiovasc Res.*, May 2003, 58(2):336-50.

Folkman, "Therapeutic angiogenesis in ischemic limbs", *Circulation*, Mar. 1998, 97(12):1108-10.

Iwaguro et al., "Endothelial progenitor cell vascular endothelial growth factor gene transfer for vascular regeneration", *Circulation,*, Feb. 2002, 105(6):732-8.

* cited by examiner

INTRAMYOCARDIAL INJECTION OF AUTOLOGOUS BONE MARROW

CROSS-REFERENCE TO RELATED APPLICATIONS

This application is a national stage application of international application PCT/US00/08353, filed 30 Mar. 2000, which claims benefit to U.S. Provisional Application Nos. 60/126,800, filed 30 Mar. 1999, and 60/138,379, filed 9 Jun. 1999.

FIELD OF THE INVENTION

This application is directed to a method of injecting autologous bone marrow. More specifically, this invention is directed to intramyocardial injection of autologous bone marrow to enhance collateral blood vessel formation and tissue perfusion.

BACKGROUND OF THE INVENTION

The use of recombinant genes or growth-factors to enhance myocardial collateral blood vessel function may represent a new approach to the treatment of cardiovascular disease. Kornowski, R., et al., "Delivery strategies for therapeutic myocardial angiogenesis", *Circulation* 2000; 101:454–458. Proof of concept has been demonstrated in animal models of myocardial ischemia, and clinical trials are underway. Unger, E. F., et al., "Basic fibroblast growth factor enhances myocardial collateral flow in a canine model", *Am J Physiol* 1994; 266:H1588–1595; Banai, S. et al., "Angiogenic-induced enhancement of collateral blood flow to ischemic myocardium by vascular endothelial growth factor in dogs", *Circulation* 1994; 83–2189; Lazarous, D. F., et al., "Effect of chronic systemic administration of basic fibroblast growth factor on collateral development in the canine heart", *Circulation* 1995; 91:145–153; Lazarous, D. F., et al., "Comparative effects of basic development and the arterial response to injury", *Circulation* 1996; 94:1074–1082; Giordano, F. J., et al., "Intracoronary gene transfer of fibroblast growth factor-S increases blood flow and contractile function in an ischemic region of the heart", *Nature Med* 1996; 2:534–9. Most strategies for trans-catheter delivery of angiogenic factors have employed an intracoronary route which may have limitations due to imprecise localization of genes or proteins and systemic delivery to non-cardiac tissue. Thus, it would be desirable to have the capacity for direct delivery of angiogenic factors or genes to precisely defined regions of the myocardium rather than to the entire heart, and to minimize the potential for systemic exposure. Guzman, R. J., et al., "Efficient gene transfer into myocardium by direct injection of adenovirus vectors", *Circ Res* 1993; 73:1202–7; Mack, C. A., et al., "Biologic bypass with the use of adenovirus-mediated gene transfer of the complementary deoxyribonucleic acid for VEGF-121, improves myocardial perfusion and function in the ischemic porcine heart", *J Thorac Cardiovasc Surg* 1998;115:168–77.

The effect of direct intra-operative intramyocardial injection of angiogenic factors on collateral function has been studied in animal models of myocardial ischemia. Open chest, transepicardial administration of an adenoviral vector containing a transgene encoding an angiogenic peptide resulted in enhanced collateral function. (Mack et al., supra.) Angiogenesis was also reported to occur with direct intramyocardial injection of an angiogenic peptide or a plasmid vector during open heart surgery in patients. Schumacher, B., et al., "Induction of neoangiogenesis in ischemic myocardium by human growth factors. First clinical results of a new treatment of coronary heart disease", *Circulation* 1998; 97:645–650; Losordo, D. W., et al., "Gene therapy for myocardial angiogenesis: initial clinical results with direct myocardial injection of phVEGF165 as sole therapy for myocardial ischemia", *Circulation* 1998; 98:2800.

Despite the promising hope for therapeutic angiogenesis as a new modality to treat patients with coronary artery disease, there is still a huge gap regarding what specific strategy will optimally promote a clinically relevant therapeutic angiogenic response. Moreover, it is unclear which one (or more) out of multiple angiogenic growth factors may be associated with a beneficial angiogenic response. In addition, the use of different tissue delivery platforms, e.g., proteins, adenovirus, or "naked" DNA, to promote the optimal angiogenic response has remained an open issue.

OBJECTS OF THE INVENTION

It is an object of this invention to provide a novel therapeutic modality wherein autologous bone marrow is injected to promote angiogenesis in the injected tissue.

It is also an object of this invention to provide a novel method of intramyocardial injection to enhance collateral blood vessel formation and tissue perfusion.

These and other objects of the invention will become more apparent in the discussion below.

SUMMARY OF THE INVENTION

Most currently tested therapeutic approaches have focused on a single angiogenic growth factor (e.g., VEGF, FGF, angiopoietin-1) delivered to the ischemic tissue. This can be accomplished either by delivery of the end-product (e.g., protein) or by gene transfer, using diverse vectors. However, it is believed that complex interactions among several growth factor systems are probably necessary for the initiation and maintenance of new blood vessel formation. More specifically, it is believed important to induce a specific localized angiogenic milieu with various angiogenic cytokines interacting in concert and in a time-appropriate manner to initiate and maintain the formation and function of new blood vessels.

The bone marrow (BM) is a natural source of a broad spectrum of cytokines and cells that are involved in the control of angiogenic processes. It is therefore believed that the intramyocardial injection of autologous (A) BM, by taking advantage of the natural ability of these cells to secrete many angiogenic factors in a time-appropriate manner, provides an optimal intervention for achieving therapeutic collateral development in ischemic myocardium.

According to the invention autologous bone marrow is injected, either as a "stand alone" therapeutic agent or combined with any pharmacologic drug, protein or gene or any other compound or intervention that may enhance bone marrow production of angiogenic growth factors and/or promote endothelial cell proliferation, migration, and blood vessel tube formation. The "combined" agent(s) can be administered directly into the patient or target tissue, or incubated ex-vivo with bone marrow prior to injection of bone marrow into the patient. Non-limiting examples of these "combined" agents are Granulocyte-Monocyte Colony Stimulatory Factor (GM-CSF), Monocyte Chemoattractant Protein 1 (MCP-1), and Hypoxia Inducible Factor-1 (HIF-1). An example of an intervention that may enhance bone marrow production of angiogenic factors is ex-vivo exposure of bone marrow cells to hypoxia. The autologous bone marrow, alone or with "combined" agents, can be delivered to the patient directly via either trans-endocardial or trans-epicardial approaches into either ischemic and/or non-ischemic myocardium, or directly into any other ischemic organ (including a peripheral limb) to enhance and/or promote the development of collateral blood vessel formation and therefore collateral flow to ischemic myocardium or ischemic limbs. This approach can also be used to promote the development of newly implanted dedifferentiated and/or differentiated myocardial cells by the process of cardiac myogenesis.

The invention comprises various autologous bone marrow transplantation strategies to enhance angiogenesis and/or myogenesis and thereby accelerate the development of new blood vessels into ischemic myocardium or lower extremities. Another aspect of the invention concerns the strategy of "optimization of angiogenic gene expression." This strategy employs co-administration of HIF-1 with the autologous bone marrow. HIF-1 is a transcription factor known to be induced and activated by hypoxia, and known to induce expression of multiple genes involved in the response to hypoxia. A similar approach involves the exposure of autologous bone marrow to endothelial PAS domain protein 1 (EPAS1). EPAS1 shares high structural and functional homology with HIF-1. The strategy also involves the ex-vivo exposure of the bone marrow to hypoxia to increase the production of vascular endothelial growth factor (VEGF) expression or other cytokines with proven angiogene activity (such as MCP-1) prior to its direct injection into the heart or any peripheral ischemic tissue. This invention thus includes the direct intramyocardial (trans-epicardial or trans-endocardial) or peripheral intramuscular injection of autologous bone marrow; stimulated autologous bone marrow, for example, stimulated by HIF-1, EPAS1, MCP-1, GM-CSF, or transient exposure to hypoxia or other forms of energy, such as ultrasound, RF, electromagnetic or laser energy; or autologous bone marrow product derived from conditioned medium (acellular component/s of cultured bone marrow). The stimulation of the bone marrow could be by the direct exposure of the bone marrow to the factors in the form of proteins, or the bone marrow cells can be transfected with vectors carrying the relevant genes. For example, bone marrow can be transfected with a plasmid vector, or with an adenoviral vector, carrying the HIF-1 or EPAS1 transgenes.

DETAILED DESCRIPTION OF THE INVENTION

Figure 1:
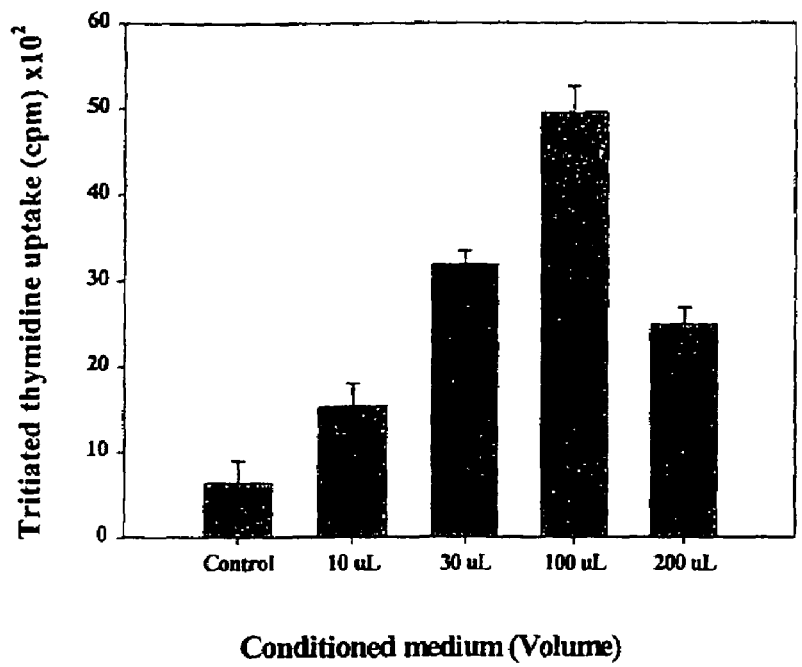
FIG. 1 is a graph of the proliferation of PAEC's vs. the quantities of conditioned medium.

Bone marrow is a natural source of a broad spectrum of cytokines that are involved in the control of angiogenic and inflammatory processes. The cytokines expressed comprise mediators known to be involved in the maintenance of early and late hematopoiesis (IL-1 alpha and IL-1 beta, IL-6, IL-7, IL-8, IL-11 and IL-13; colony-stimulating factors, thrombopoietin, erythropoietin, stem cell factor, flt 3-ligand, hepatocyte cell growth factor, tumor necrosis factor alpha, leukemia inhibitory factor, transforming growth factors beta 1 and beta 3; and macrophage inflammatory protein 1 alpha), angiogenic factors (fibroblast growth factors 1 and 2, vascular endothelial growth factor) and mediators whose usual target (and source) is the connective tissue-forming cells (platelet-derived growth factor A, epidermal growth factor, transforming growth factors alpha and beta 2, oncostatin M and insulin-like growth factor-1), or neuronal cells (nerve growth factor). Sensebe, L., et al., *Stem Cells* 1997; 15:133–43. Moreover, it has been shown that VEGF polypeptides are present in platelets and megacaryocytes, and are released from activated platelets together with the release of beta-thromboglobulin. Wartiovaara, U., et al., *Thromb Haemost* 1998; 80:171–5; Mohle, R., *Proc Natl Acad Sci USA* 1997; 94:663–8.

There are also indicators to support the concept that angiogenesis is needed to support bone marrow function and development of hematopoietic cells, including stem cells and progenitor cells, that may enter the circulation and target to sites of wound healing and/or ischemia, ultimately contributing to new blood vessel formation. Monoclonal antibodies that specifically recognize undifferentiated mesenchymal progenitor cells isolated from adult human bone marrow have been shown to recognize cell surface markers of developing microvasculature, and evidence suggests such cells may play a role in embryonal angiogenesis. Fleming, J. E., Jr., *Dev Dyn* 1998; 212:119–32.

Bone marrow angiogensis may become exaggerated in pathologic states where the bone marrow is being activated by malignant cells (such as in multiple myeloma) where bone marrow angiogenesis has been shown to increase simultaneously with progression of human multiple myeloma cells. Ribatti, D., et al., *Br J Cancer* 1999; 79:451–5. Moreover, vascular endothelial growth factor (VEGF) has been shown to play a role in the growth of hematopoietic neoplasms such as multiple myeloma, through either a paracrine or an autocrine mechanism. Bellamy, W. T., *Cancer Res* 1999; 59:728–33; Fiedler, W., *Blood* 1997; 89:1870–5). It is believed that autologous bone marrow, with its unique native humoral and cellular properties, is a potential source of various angiogenic compounds. This natural source of "mixed" angiogenic cytokines can surprisingly be utilized as a mixture of potent interactive growth factors to produce therapeutic angiogenesis and/or myogenesis; use of the cells per se could provide a more sustained source of these natural angiogenic agents.

One of the factors that most likely participates in initiating angiogenesis in response to ischemia is HIF-1, a potent transcription factor that binds to and stimulates the promoter of several genes involved in responses to hypoxia. Induction and activation of HIF-1 is tightly controlled by tissue pO2; HIF-1 expression increases exponentially as pO2 decreases, thereby providing a positive feedback loop by which a decrease in pO2 causes an increase in the expression of gene products that serve as an adaptive response to a low oxygen environment. Activation of HIF-1 leads, for example, to the induction of erythropoietin, genes involved in glycolysis, and to the expression of VEGF. It probably also modulates the expression of many other genes that participate in the adaptive response to low pO2 levels. The mechanism by which HIF-1 regulates levels of proteins involved in the response to hypoxia is through transcriptional regulation of genes responding to low pO2. Thus, such genes have short DNA sequences within the promoter or enhancer regions that contain HIF-1 binding sites, designated as hypoxia responsive elements (HRE). HIF-1 is a heterodimer with a basic helix-loop-helix motif, consisting of the subunits HIF-1α and HIF-1β. Its levels are regulated by pO2 both transcriptionally and posttranscriptionally—HIF-1 induction is increased by hypoxia, and its half-life is markedly reduced as pO2 levels increase.

It is relevant that while expression of HIF-1 (as determined in HeLa cells) is exponentially and inversely related to pO2, the inflection point of the curve occurs at an oxygen saturation of 5%, with maximal activity at 0.5% and ½ maximal activity at 1.5–2.0%. These are relatively low levels of hypoxia, and it is not clear whether such levels occur in the presence of mild levels of myocardial or lower limb ischemia—i.e., levels present in the absence of tissue necrosis (myocardial infarction, and leg ulcerations, respectively). Thus, bone marrow cells could have the capacity to secrete angiogenic factors and thereby enhance collateral development. However, it is possible that such activity may not become manifest in the specific tissue environments treated unless some additional stimulus is present. It is, therefore, a preferred aspect of the invention to co-administer, if necessary, bone marrow implant with HIF-1. It is anticipated that HIF-1 will provide optimal expression of many of the hypoxia-inducible angiogenic genes present in the bone marrow implant. The HIF-1 can be injected either as the protein, or as the gene. If as the latter, it can be injected either in a plasmid or viral vector, or any other manner that leads to functionally relevant protein levels. For example, bone marrow can be transfected, ex vivo, with a plasmid vector, or with an adenoviral vector, carrying the HIF-1 or EPSA1 transgenes. It is emphasized, however, that HIF-1 is used in this section as an example of an intervention that could enhance production of angiogenic substances by bone marrow. This invention also covers use of other agents, which by enhancing HIF-1 activity (i.e., prolonging its half-life), or by producing effects analgous to HIF-1, stimulate the bone marrow to increase expression of angiogenic factors. A similar approach involves the exposure of autologous bone marrow to endothelial PAS domain protein 1 (EPAS1). EPAS1 shares high structural and functional homology with HIF-1.

Because VEGF promoter activity is enhanced by HIF-1, this invention also includes the ex-vivo exposure of bone marrow cells in culture to hypoxia or other forms of energy, such as, for example, ultrasound, RF, or electromagnetic energy. This intervention increases VEGF and other gene expression. By this effect it may augment the capacity of bone marrow to stimulate angiogenesis.

Another aspect of the invention involves the ex-vivo stimulation of aspirated autologous bone marrow by HIF-1 (or products that augment the effects of HIF-1 or produce similar effects to HIF-1 on bone marrow) or direct exposure of bone marrow to hypoxic environment followed by the delivery of activated bone marrow cells to the ischemic myocardium or peripheral organ (e.g., ischemic limb) to enhance collateral-dependent perfusion in cardiac and/or peripheral ischemic tissue. The stimulation of the bone marrow could be by the direct exposure of the bone marrow to the factors in the form of proteins, or the bone marrow cells can be transfected with vectors carrying the relevant genes. For example, bone marrow can be transfected with a plasmid vector, or with an adenoviral vector, carrying the HIF-1 or EPAS1 transgenes.

Current data indicate the importance of monocyte-derived cytokines for enhancing collateral function. Monocytes are activated during collateral growth in vivo, and monocyte chemotactic protein-1 (MCP-1) is upregulated by shear stress in vitro. It has been shown that monocytes adhere to the vascular wall during collateral vessel growth (arteriogenesis) and capillary sprouting (angiogenesis). MCP-1 was also shown to enhance collateral growth after femoral artery occlusion in the rabbit chronic hindlimb ischemia model (Ito et al., *Circ Res* 1997; 80:829–3). Activation of monocytes seems to play an important role in collateral growth as well as in capillary sprouting. Increased monocyte recruitment by LPS is associated with increased capillary density as well as enhanced collateral and peripheral conductance at 7 days after experimental arterial occlusion (Arras M. et al., *J Clin Invest* 1998;101:40–50.)

A further aspect of the invention involves the ex-vivo stimulation of aspirated autologous bone marrow by MCP-1, followed by the direct delivery of activated bone marrow cells to the ischemic myocardium or peripheral organ (e.g., ischemic limb) to enhance collateral-dependent perfusion and muscular function in cardiac and/or peripheral ischemic tissue. The stimulation of the bone marrow could be by the direct exposure of the bone marrow to MCP-1 in the form of the protein, or the bone marrow cells can be transfected with a vector carrying the MCP-1 gene. For example, bone marrow can be transfected with a plasmid vector, or with an adenoviral vector, carrying the MCP-1 transgene.

Granulocyte-macrophage colony-stimulating factor (GM-CSF) and Granulocyte-Colony Stimulatory Factor (G-CSF) are stimulatory cytokines for monocyte maturation and are multipotent hematopoietic growth factors, which are utilized in clinical practice for various hematological pathologies such as depressed white blood cell count (i.e., leukopenia or granulocytopenia or monocytopenia) which occurs usually in response to immunosuppressive or chemotherapy treatment in cancer patients. GM-CSF has also been described as a multilineage growth factor that induces in vitro colony formation from erythroid burst-forming units, eosinophil colony-forming units (CSF), and multipotential (CSF), as well as from granulocyte-macrophage CSF and granulocyte CFU. (Bot F. J., *Exp Hematol* 1989, 17:292–5). Ex-vivo exposure to GM-CSF has been shown to induce rapid proliferation of CD-34+ progenitor cells (Egeland T. et al., *Blood* 1991; 78:3192–9.) These cells have the potential to differentiate into vascular endothelial cells and may naturally be involved in postnatal angiogenesis. In addition, GM-CSF carries multiple stimulatory effects on macrophage/monocyte proliferation, differentiation, motility and survival (reduced apoptotic rate). Consistent with the combined known effects on bone marrow derived endothelial progenitor cells and monocytes, it is another aspect of the invention to use GM-CSF as an adjunctive treatment to autologous bone marrow injections aimed to induce new blood vessel formation and differentiation in ischemic cardiovascular organs. Moreover, GM-CSF may further enhance therapeutic myocardial angiogenesis caused by bone marrow, by augmenting the effect of bone marrow, or by further stimulating, administered either in vivo or in vitro, bone marrow that is also being stimulated by agents such as HIF-1, EPAS1, hypoxia, or MCP-1.

In the examples below, certain testing regarding aspects of the invention is set forth. These examples are non-limitative.

EXAMPLES

Example 1

Effect of Bone Marrow Cultured Media on Endothelial Cell Proliferation

Studies were conducted to determine whether aspirated pig autologous bone marrow cells obtained secreted VEGF, a potent angiogenic factor, and MCP-1, which recently has been identified as an important angiogenic co-factor. Bone marrow was cultured in vitro for four weeks. The conditioned medium was added to cultured pig aortic endothelial cells (PAECs), and after four days proliferation was assessed. VEGF and MCP-1 levels in the conditioned medium were assayed using ELISA. During the four weeks in culture, BM cells secreted VEGF and MCP-1, such that their concentrations increased in a time-related manner. The resulting conditioned medium enhanced, in a dose-related manner, the proliferation of PAECs. The results indicate that BM cells are capable of secreting potent angiogenic cytokines such as VEGF and MCP-1 and of inducing proliferation of vascular endothelial cells.

Pig Bone Marrow Culture

Bone marrow (BM) cells were harvested under sterile conditions from pigs with chronic myocardial ischemia in preservative free heparin (20 units/ml BM cells) and filtered sequentially using 300μ and 200μ stainless steel mesh filters. BM cells were then isolated by Ficoll-Hypaque gradient centrifugation and cultured in long-term culture medium (LTCM) (Stem Cell Tech, Vancouver, British Columbia, Canada) at 330° C. with 5% $CO_2$ in T-25 culture flask. The seeding density of the BMCs in each culture was 7×106/ml. Weekly, one half of the medium was removed and replaced with fresh LTCM. The removed medium was filtered (0.2μ filter) and stored at −200° C. for subsequent Enzyme-linked Immunosorbent Assay (ELISA) and cell proliferation assays.

Isolation and Culture of Pig Aortic Endothelial Cells

Fresh pig aortic endothelial cells (PAECs) were isolated using conventional methods. Endothelial cell growth medium (EGM-2 medium, Clonetics, San Diego, Calif.), containing 2% FBS, hydrocortisone, human FGF, VEGF, human EGF, IGF, heparin and antibiotics, at 37° C. with 5% carbon dioxide. When the cells became confluent at about 7 days, they were split by 2.5% trypsin and cultured thereafter in medium 199 with 10% FBS. Their identity was confirmed by typical endothelial cell morphology and by immunohistochemistry staining for factor VIII. Passage 3–10 were used for the proliferation study.

Effects of Conditioned Medium on Aortic Endothelial Cells

Cell proliferation assay: PAECs (Passage 3–10) were removed from culture flasks by trypsinization. The detached cells were transferred to 96-well culture plates and plated at a seeding density of 5,000 cells/well. Cells were cultured for 2–3 days before being used in proliferation and DNA synthesis experiments. The conditioned medium of BM cells cultures were collected at 4 weeks; medium from 7 culture flasks were pooled and used in the bioassay. Aliquotes (10 μL, 30 μL, 100 μL or 200 μL) of pooled conditioned medium, or LTCM (200 μL, as control), were added to confluent PAECs in 96-well plates in triplicate. Four days following culture with conditioned medium or control medium, the PAECs were trypsinized and counted using a cell counter (Coulter Counter Beckman Corporation, Miami Fla.).

Effects of Conditioned Medium on PAEC DNA Synthesis

Aliquotes (10 μL, 30 μL, 100 μL or 200 μL) of conditioned medium from pooled samples or control medium (LTCM, 200 μL) were added to PAECs in 96-well plate (same seeding density as above) in triplicate. After 2 days, 1 μCi tritiated thymidine was added to each well. Forty-eight hours later, DNA in PAECs was harvested using a cell harvester (Mach III M Tomtec, Hamden, Conn.) and radioactivity was counted by liquid scintillation counter (Multidetector Liquid Scintillance Luminescence Counter EG&G Wallac, Turku, Finland).

Determination of VEGF and MCP-1 in Conditioned Medium by ELISA VEGF

The concentration of VEGF in conditioned medium was measured using a sandwich ELISA kit (Chemicon International Inc., Temecula, Calif.). Briefly, a plate pre-coated with anti-human VEGF antibody was used to bind VEGF in the conditioned medium or to a known concentration of recombinant VEGF. The complex was detected by the biotinylated anti-VEGF antibody, which binds to the captured VEGF. The biotinylated VEGF antibody in turn was detected by streptavidin-alkaline phosphatase and color generating solution. The anti-human VEGF antibody cross-reacts with porcine VEGF.

Determination of MCP-1 in Conditioned Medium by ELISA

The concentration of MCP-1 in conditioned medium was assayed by sandwich enzyme immunoassay kit (R & D Systems, Minneapolis, Minn.): a plate pre-coated with anti human MCP-1 antibody was used to bind MCP-1 in the conditioned medium or to a known concentration of recombinant protein. The complex was detected by the biotinylated anti-MCP-1 antibody, which binds to the captured MCP-1. The biotinylated MCP-1 antibody in turn was detected by streptavidin-alkaline phosphatase and color generating solution. The anti-human MCP-1 antibody cross-reacts with porcine MCP-1.

Results

The BM conditioned medium collected at four weeks increased, in a dose-related manner, the proliferation of PAECs (FIG. 1). This was demonstrated by counting the number of cells directly and by measuring tritiated thymidine uptake (p<0.001 for both measurements). The dose-related response demonstrated a descending limb; proliferation decreased with 200 μL conditioned medium compared to 30 μL and 100 μL (P 0.003 for both comparisons). Similar dose-related results were observed in the tritiated thymidine uptake studies (P=0.03 for 30 μL and 100 μL compared to 200 μL, respectively).

Figure 2:
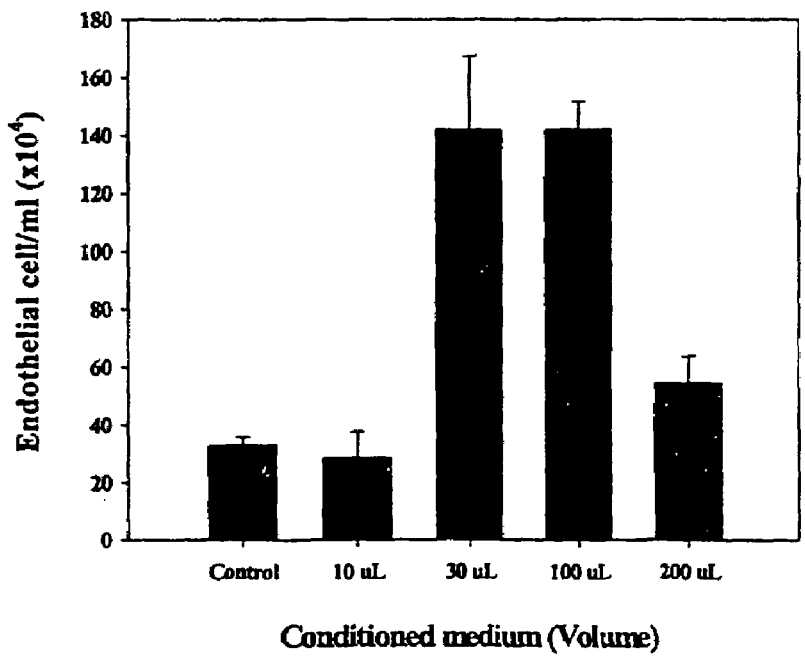
FIG. 2 is a graph of the proliferation of endothelial cells vs. the quantities of conditioned medium.

A limited number (5±4%) of freshly aspirated BM cells stained positive for factor VIII. The results are set forth in FIG. 2. This contrasted to 57±14% of the adherent layer of BM cells cultured for 4 weeks, of which 60±23% were endothelial-like cells and 40±28% appeared to be megakaryocytes.

Figure 3:
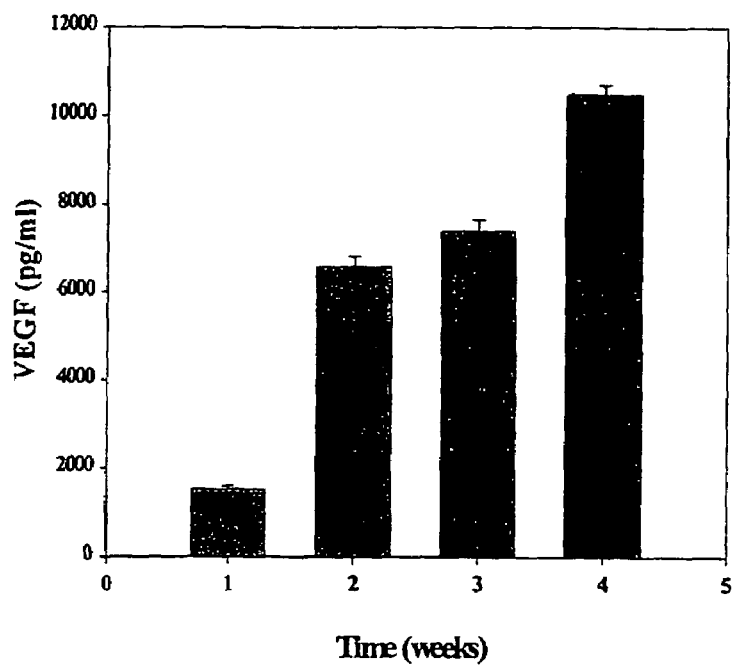
FIG. 3 is a graph of the concentration of VEGF in conditioned medium over a four-week period of time.
Figure 4:
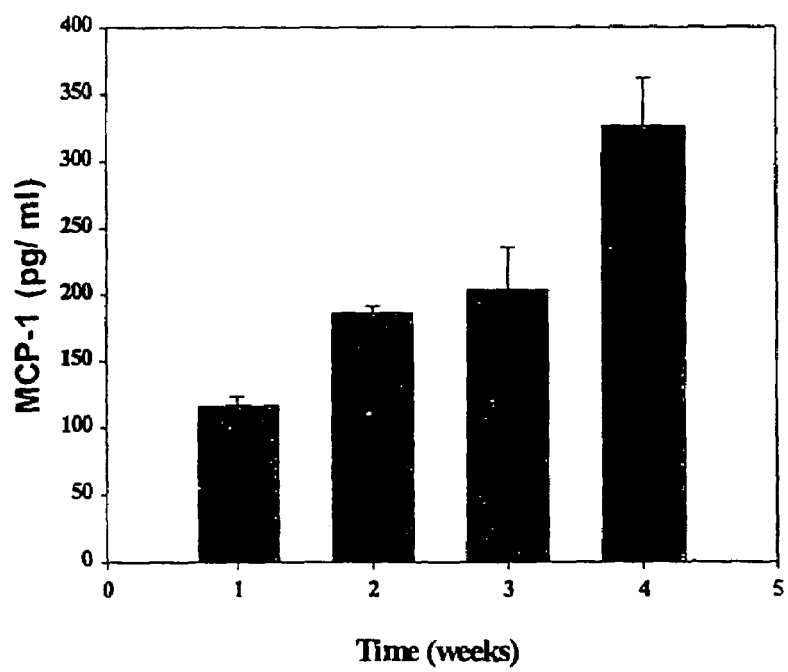
FIG. 4 is a graph of the concentration of MCP-1 in conditioned medium over a four-week period of time.

Over a 4-week period, the concentrations of VEGF and MCP-1 in the BM conditioned medium increased gradually to 10 and 3 times the 1st week level, respectively (P<0.001 for both comparisons) (FIG. 3). In comparison, VEGF and MCP-1 levels in a control culture medium, not exposed to BM, were 0 and 11±2 pg/ml, respectively, as shown in FIG. 4.

Example 2

Effects of Hypoxia on VEGF Secretion by Cultured Pig Bone Marrow Cells

It was demonstrated that hypoxia markedly increases the expression of VEGF by cultured bone marrow endothelial cells, results indicating that ex-vivo exposure to hypoxia, by increasing expression of hypoxia-inducible angiogenic factors, can further increase the collateral enhancing effect of bone marrow cells and its conditioned media to be injected in ischemic muscular tissue. Pig bone marrow was harvested and filtered sequentially using 300μ and 200μ stainless steel mesh filters. BMCs were then isolated by Ficoll-Hypaque gradient centrifugation and cultured at 33° C. with 5% $CO_2$ in T-75 culture flasks. When cells became confluent at about 7 days, they were split 1:3 by trypsinization. After 4 wks of culture, the BMCs were either exposed to hypoxic conditions (placed in a chamber containing 1% oxygen) for 24 to 120 hrs, or maintained under normal conditions. The resulting conditioned medium was collected and VEGF, MCP-1 were analyzed by ELISA.

Exposure to hypoxia markedly increased VEGF secretion: At 24 hrs VEGF concentration increased from 106±13 pg/ml under normoxic, to 1,600±196 pg/ml under hypoxic conditions (p=0.0002); after 120 hrs it increased from 4,163±62 to 6,028±167 pg/ml (p<0.0001). A separate study was performed on freshly isolated BMCs, and the same trend was found. Hypoxia also slowed the rate of proliferation of BMCs. MCP-1 expression was not increased by hypoxia, a not unexpected finding as its promoter is not known to have HIF binding sites.

Example 3

Effect of Bone Marrow Cultured Media on Endothelial Cell Tube Formation

It was demonstrated, using pig endothelial cells and vascular smooth muscle cells co-culture technique, that the conditioned medium of bone marrow cells induced the formation of structural vascular tubes in vitro. No such effect on vascular tube formation was observed without exposure to bone marrow conditioned medium. The results suggest that bone marrow cells and their secreted factors exert pro-angiogenic effects.

Example 4

The effect of Transendocardial Delivery of Autologous Bone Marrow on Collateral Perfusion and Regional Function in Chronic Myocardial Ischemia Model Chronic myocardial ischemia was created in 14 pigs by the implantation of ameroid constrictors around the left circumflex coronary artery. Four weeks after implantation, 7 animals underwent transendocardial injections of freshly aspirated ABM into the ischemic zone using a transendocardial injection catheter (2.4 ml per animal injected at 12 sites) and 7 control animals were injected with heparinized saline. At baseline and 4 weeks later, animals underwent rest and pacing echocardiogram to assess regional contractility (% myocardial thickening), and microsphere study to assess collateral-dependent perfusion at rest and during adenosine infusion. Four weeks after injection of ABM collateral flow (expressed as the ratio of ischemic/normal zone×100) improved in ABM-treated pigs but not in controls (ABM: 95±13 vs 81±11 at rest, P=0.017; 85±19 vs 72±10 during adenosine, P=0.046; Controls: 86±14 vs 86±14 at rest, P=NS; 73±17 vs 72±14 during adenosine, P=0.63). Similarly, contractility increased in ABM-treated pigs but not in controls (ABM: 83±21 vs 60±32 at rest, P=0.04; 91±44 vs 35±43 during pacing, P=0.056, Controls: 69±48 vs 64±46 at rest, P=0.74; 65±56 vs 37±56 during pacing, P=0.23).

The results indicate that catheter-based transendocardial injection of ABM can augment collateral perfusion and myocardial function in ischemic myocardium, findings suggesting that this approach may constitute a novel therapeutic strategy for achieving optimal therapeutic angiogenesis.

Fourteen specific-pathogen-free domestic pigs weighing approximately 70 kg were anesthetized, intubated, and received supplemental $O_2$ at 2 L/min as well as 1–2% isoflurene inhalation throughout the procedure. Arterial access was obtained via right femoral artery isolation and insertion of an 8 French sheath. The left circumflex artery was isolated through a left lateral thoracotomy and a metal encased ameroid constrictor was implanted at the very proximal part of the artery. Four weeks after the ameroid constrictor implantation all pigs underwent (1) a selective left and right coronary angiography for verification of ameroid occlusion and assessment of collateral flow; (2) transthoracic echocardiography studies; and (3) regional myocardial blood flow assessment.

Bone Marrow Aspiration and Preparation and Intramyocardial Injection

Immediately after completion of the baseline assessment, all animals underwent BM aspiration from the left femoral shaft using standard techniques. BM was aspirated from 2 sites (3 ml per site) using preservative free heparinized glass syringes (20 unit heparin/1 ml fresh BM). The aspirated bone marrow was immediately macro-filtered using 300% and 200μ stainless steel filters, sequentially. Then, the bone marrow was injected using a trans-endocardial injection catheter into the myocardium in 12 sites (0.2 ml per injection site for total of 2.4. ml) directed to the ischemic myocardial territory and its borderline region.

Echocardiography Study

Transthoracic echocardiography images of short and long axis views at the mid-papillary muscle level were recorded in animals at baseline and during pacing, at baseline and during follow-up evaluation at four weeks after ABM implantation. Fractional shortening measurements were obtained by measuring the % wall thickening (end-systolic thickness minus end-diastolic thickness/end-diastolic thickness)×100. Those measurements were taken from the ischemic territory (lateral area) and remote territory (anterior-septal area). Subsequently, a temporary pacemaker electrode was inserted via a right femoral venous sheath and positioned in the right atrium. Animals were paced at 180/minute for 2 minutes and echocardiographic images were simultaneously recorded.

Regional Myocardial Blood Flow

Regional myocardial blood flow measurements were performed at rest and during maximal coronary vasodilation by use of multiple fluorescent colored microspheres (Interactive Medical Technologies, West Los Angels, Calif.) and quantified by the reference sample technique (Heymann Mass., et al., *Prog Cardiovasc Dis* 1977;20:55–79). Fluorescent microspheres (0.8 ml, 5×10$^6$ microspheres/ml, 15 μm diameter in a saline suspension with 0.01% Tween 80) were injected into the left atrium via a 6F Judkins left 3.5 diagnostic catheter. Maximal coronary vasodilation was induced by infusing adenosine at a constant rate of 140

μg/kg/min (Fujisawa USA, Deerfield, Ill.) into the left femoral vein over a period of 6 minutes. During the last 2 minutes of the infusion, microsphere injection and blood reference withdrawal were undertaken in identical fashion to the rest study.

Following completion of the perfusion assessment, animals were sacrificed with an overdose of sodium pentobarbital and KCL. Hearts were harvested, flushed with Ringer Lactate, perfusion-fixed for 10–15 minutes, and subsequently immersion-fixed with 10% buffered formaldehyde for 3 days. After fixation was completed, the hearts were cut along the short axis into 7-mm thick slices. The 2 central slices were each divided into 8 similar sized wedges, which were further cut into endocardial and epicardial subsegments. The average of 8 lateral ischemic zone and 8 septal normal zone sub-segments measurements were used for assessment of endocardial and epicardial regional myocardial blood flow. The relative collateral flow was also computed as the ratio of the ischemic zone/non ischemic zone (IZ/NIZ) blood flow.

Histopathology

To assess whether injecting BM aspirate via the use of an injection catheter was associated with mechanical cell damage, standard BM smears were prepared before and after propelling the freshly filtered ABM aspirate through the needle using similar injecting pressure as in the in-vivo study. Morphological assessment was performed by an independent experienced technician who was blinded to the study protocol.

Histopathology assessment was performed on sampled heart tissue. In the pilot study, 7-mm thick short-axis slices were examined under UV light to identify fluorescent-tagged areas. Each identified area was cut into 3 full thickness adjacent blocks (central, right and left) that were immersion-fixed in 10% buffered formaldehyde. Subsequently, each such block was cut into 3 levels, of which 2 were stained with Hematoxylin and Eosin (H&E) and one with PAS. In addition, one fresh fluorescent-labeled tissue block was obtained from the ischemic region of each animal and was embedded in OCT compound (Sakura Finetek USA Inc., Torance, Calif.) and frozen in liquid nitrogen. Frozen sections of these snap-frozen myocardial tissue were air dried and fixed with aceton. Immunoperoxidase stain was performed with the automated Dako immunno Stainer (Dako, Carpenteria, Calif.). The intrinsic peroxidase and non-specific uptake were blocked with 0.3% hydrogen peroxidase and 10% ovo-albumin. Monoclonal mouse antibody against CD-34 (Becton Dickinson, San Jose, Calif.) was used as the primary antibody. The linking antibody was a biotinylated goat anti-mouse IgG antibody and the tertiary antibody was strepavidin conjugated with horse reddish peroxidase. Diaminobenzidine (DAB) was used as the chromogen and the sections were counterstained with 1% methylgreen. After dehydration and clearing, the slides were mounted and examined with a Nikon Labphot microscop.

In the efficacy study, full-thickness, 1.5 square centimeter sections from the ischemic and non-ischemic regions were processed for paraffin sections. Each of the samples was stained with H&E, Masson's trichrome, and factor VIII related antigen. The immunoperoxidase stained slides were studied for density of endothelial cell population and vascularization. The latter was distinguished from the former by the presence of a lumen. Vascularity was assessed using 5 photomicrographs samples of the factor VIII stained slides taken from the inner half of the ischemic and non-ischemic myocardium. Density of endothelial cells was assessed using digitized images of the same photomicrographs. The density of the endothelial population was determined by Sigma-Scan Pro morphometry software using the intensity threshold method. The total endothelial area for each sample as well as for each specimen were obtained along with the relative percent endothelial area (endothelial area/area of the myocardium studied). The total endothelial area was also calculated as the relative percent of the non-infarcted (viable) area of the myocardium studied. The trichrom stained sections were digitized and the area occupied by the blue staining collagen as well as the total area of the section excluding the area occupied by the epicardium (which normally contained collagen) were measured using Sigma-Scan Pro. The infarcted area was then calculated as the area occupied by the blue staining.

Procedural Data

Intra-myocardial injections either with ABM or placebo were not associated with any acute change in mean blood pressure, heart rate or induction of arrhythmia. All hemodynamic parameters were comparable between the two groups. Pair-wise comparison showed similar hemodynamic parameters within each group in the index compared to the follow-up procedure except for higher initial mean arterial blood pressure at follow-up in the control group (P=0.03) with no subsequent differences during pacing or adenosine infusion.

Myocardial Function

Regional myocardial function assessment is shown in Table I below. Pre-intervention relative fractional wall thickening, expressed as ischemic zone to non-ischemic zone (IZ/NIZ) ratio×100, at rest and during pacing, was similar between groups (P=0.86 and 0.96, respectively). At 4 weeks following the intra-myocardial injection of ABM, improved regional wall thickening occurred at rest and during pacing, which was due to an ~50% increase in wall thickening of the collateral-dependent ischemic lateral wall. No significant changes were observed in the control animals, although a trend towards improvement in wall thickening was noted in the ischemic area during pacing at follow-up.

TABLE I

Regional Contractility of the Ischemic Wall

|  | Baseline | Follow-up | P |
|---|---|---|---|
| Rest |  |  |  |
| ABM (%) | 60 ± 32 | 83 ± 21 | 0.04 |
| Control (%) | 64 ± 46 | 69 ± 48 | 0.74 |
| Pacing |  |  |  |
| ABM (%) | 36 ± 43 | 91 ± 44 | 0.056 |
| Control (%) | 37 ± 56 | 65 ± 56 | 0.23 |

ABM indicates autologous bone marrow.

Myocardial Perfusion Data

Regional myocardial perfusion assessment is shown in Table II below. There were no differences between the treated and control groups in the pre-intervention relative transmural myocardial perfusion, IZ/NIZ, at rest and during adenosine infusion (P=0.42 and 0.96, respectively). At 4 weeks following ABM injection, relative regional transmural myocardial perfusion at rest and during pacing improved significantly. This was due to an absolute improvement in myocardial perfusion in the ischemic zone both at rest (an increase of 57%, P=0.08) and during adenosine infusion (37%, P=0.09), while no significant changes were noted in absolute flow to the non-ischemic zone either at rest (increase of 35%, P=0.18) or during adenosine infusion (increase of 25%, P=0.26). The increase in regional myocardial blood flow found in the ischemic zones consisted of both endocardial (73%) and epicardial (62%) regional improvement at rest, with somewhat lesser improvement during adenosine infusion (40% in both zones). At 4 weeks, the control group showed no differences in transmural, endocardial or epicardial perfusion in the ischemic and non-ischemic zones compared to pre-intervention values.

TABLE II

| Regional Myocardial Perfusion | | | |
|---|---|---|---|
| | Baseline | Follow-up | P |
| Rest | | | |
| ABM (%) | 83 ± 12 | 98 ± 14 | 0.001 |
| Control (%) | 89 ± 9 | 92 ± 0.1 | 0.43 |
| Adenosine | | | |
| ABM (%) | 78 ± 12 | 89 ± 18 | 0.025 |
| Control (%) | 77 ± 5 | 78 ± 11 | 0.75 |

ABM indicates autologous bone marrow.

Histopathology and Vascularity Assessment

Assessment of BM smears before and after passing the filtrated aspirate through the injecting catheter revealed normal structure, absence of macro-aggregates and no evidence of cell fragments or distorted cell shapes. Histopathology at day 1 following injections revealed acute lesions characterized by fibrin and inflammatory tract with dispersed cellular infiltration. The infiltrate was characterized by mononuclear cells that morphologically could not be differentiated from a BM infiltrate. Cellularity was maximal at 3 and 7 days and declined subsequently over time. At 3 weeks, more fibrosis was seen in the 0.5 ml injection-sites compared to the 0.2 ml. CD-34 immunostatining, designed to identify BM-derived progenitor cells, was performed in sections demonstrating the maximal cellular infiltrate. Overall, it was estimated that 4–6% of the cellular infiltrate showed positive immunoreactivity to CD-34.

The ischemic territory in both groups was characterized by small areas of patchy necrosis occupying overall <10% of the examined ischemic myocardium. The non-ischemic area revealed normal myocardial structure. Changes in the histomorphometric characteristics of the two groups were compared. There were no differences in the total area occupied by any blood vessel as well as the number of blood vessels >50 μm in diameter. However, comparison of the total areas stained positive for factor VIII (endothelial cells with and without lumen) in the ischemic versus the non-ischemic territories revealed differences between the 2 groups. In the ABM group, the total endothelial cell area in the ischemic collateral-dependent zone was 100% higher than that observed in the non-ischemic territory (11.6±5.0 vs. 5.7±2.3% area, P=0.016), whereas there was no significant difference in the control group (12.3±5.5 vs. 8.2±3.1% area, P=0.11). However, other parameters of vascularity, including % area occupied by any blood vessel and number of blood vessels >50 μm were similar in the ischemic and non-ischemic territories in both groups.

Example 5

The Effect of Autologous Bone Marrow Stimulated in vivo by Pre-Administration of GM-CSF in Animal Model of Myocardial Ischemia Chronic myocardial ischemia was created in 16 pigs by the implantation of ameroid constrictors around the left circumflex coronary artery. At four weeks minus 3 days after ameroid implantation, 8 animals underwent subcutaneous injection of GM-CSF for 3 consecutive days (dose 10 μg/kg per day) followed (on the fourth day and exactly 4 weeks after ameroid implantation) by transendocardial injections of freshly aspirated ABM into the ischemic zone using a transendocardial injection catheter (2.4 ml per animal injected at 12 sites) and 8 control animals without GM-CSF stimulation were injected with heparinized saline. At baseline and 4 weeks later, animals underwent rest and pacing echocardiogram to assess regional contractility (% myocardial thickening), and microsphere study to assess collateral-dependent perfusion at rest and during adenosine infusion. Four weeks after injection of ABM collateral flow (expressed as the ratio of ischemic/normal zone×100) improved in ABM-treated pigs but not in controls (ABM: 85±11 vs 72±16 at rest, P=0.026; 83±18 vs 64±19 during adenosine, P=0.06; Controls: 93±10 vs 89±9 at rest, P=0.31; 73±17 vs 75±8 during adenosine, P=0.74). Similarly, contractility increased in ABM-treated pigs but not in controls (ABM: 93±33 vs 63±27 at rest, P=0.009; 84±36 vs 51±20 during pacing, P=0.014, Controls: 72±45 vs 66±43 at rest, P=0.65; 70±36 vs 43±55 during pacing, P=0.18).

The results indicate that catheter-based transendocardial injection of ABM pre-stimulated in vivo by GM-CSF administered systemically for 3 days, can augment collateral perfusion and myocardial function in ischemic myocardium, findings suggesting that this approach may constitute a novel therapeutic strategy for achieving optimal therapeutic angiogenesis.

Example 6

Treatment of a Human Patient

Bone marrow (~5 ml) will be aspirated from the iliac crest at approximately 60 minutes prior to initiation of the cardiac procedure using preservative-free heparinized glass syringes (20 unit heparin/1 ml fresh BM). The aspirated bone marrow will be immediately macro-filtered using 300μ and 200μ stainless steel filters, sequentially. An experienced hematologist will perform the procedure under sterile conditions. The bone marrow smear will be evaluated to confirm a normal histomorphology of the bone marrow preparation.

Any of several procedures for delivery of an agent to the myocardium can be used. These include direct transepicardial delivery, as could be achieved by a surgical approach (for example, but not limited to, a transthoracic incision or transthoracic insertion of a needle or other delivery device, or via thoracoscopy), or by any of several percutaneous procedures. Following is one example of percutaneous delivery. It should be emphasized that the following example is not meant to limit the options of delivery to the specific catheter-based platform system described in the example— any catheter-based platform system can be used.

Using standard procedures for percutaneous coronary angioplasty, an introducer sheath of at least 8F is inserted in the right or left femoral artery. Following insertion of the arterial sheath, heparin is administered and supplemented as needed to maintain an ACT for 200–250 seconds throughout the LV mapping and ABM transplantation portion of the procedure. ACT will be checked during the procedure at intervals of no longer than 30 minutes, as well as at the end of the procedure to verify conformity with this requirement.

Left ventriculography is performed in standard RAO and/or LAO views to assist with guidance of NOGA-STAR™ and injection catheters, and an LV electromechanical map is obtained using the NOGA-STAR™ catheter. The 8F INJECTION-STAR catheter is placed in a retrograde fashion via the femoral sheath to the aortic valve. After full tip deflection, the rounded distal tip is gently prolapsed across the aortic valve and straightened appropriately once within the LV cavity.

The catheter (incorporating an electromagnetic tip sensor) is oriented to one of the treatment zones (e.g. anterior, lateral, inferior-posterior or other). Utilizing the safety features of the NOGA™ system, needle insertion and injection is allowed only when stability signals will demonstrate an LS value of <3. A single injection of 0.2 cc of freshly aspirated ABM will be delivered via trans-endocardial approach to the confines of up to two treatment zones with no closer than 5 mm between each injection site. The density of injection sites will depend upon the individual subject's LV endomyocardial anatomy and the ability to achieve a stable position on the endocardial surface without catheter displacement or premature ventricular contractions (PVCs).

That freshly aspirated autologous bone marrow transplanted into ischemic myocardium is associated with improved collateral flow without adverse effects may be of clinical importance for several reasons. The methodology reflected above took advantage of the natural capability of the bone marrow to induce a localized angiogenic response in an effective and apparently safe manner. Such an angiogenic strategy would probably be less costly than many others currently being tested. It would also avoid potential toxicity-related issues that are remote but definite possibilities with various gene-based approaches using viral vectors.

The invention is based on the concept that autologous bone marrow may be an optimal source for cellular (an example would be endothelial progenitor cells, but the invention is not limited to such cells as many other cells in the bone marrow may contribute importantly to the angiogenic effect) and secreted, e.g., angiogenic growth factors, elements necessary to promote new blood vessel growth and restore function when transferred to another tissue, such as ischemic heart or peripheral limbs. A patient's own bone marrow can be used as the key therapeutic source to induce therapeutic angiogensis and/or myogensis in ischemic tissues, e.g., heart muscle and/or ischemic limb, with compromised blood perfusion due to arterial obstructions. The patient's own bone marrow is aspirated, i.e., autologous bone marrow donation, processed, and injected directly into ischemia and/or adjacent non-ischemic tissue, e.g., heart muscle and/or ischemic limb, to promote blood vessel growth.

The autologous bone marrow and/or bone marrow products are injected into the heart muscle, e.g., the myocardium, by use of either a catheter-based trans-endocardial injection approach or a surgical (open chest or via thoracoscopy) trans-epicardial thoracotomy approach. Those two delivery strategies can be used to achieve the same therapeutic goal by promoting the incorporation and integration of angiogenic bone marrow elements in the target organ tissue, e.g., heart muscle and/or ischemic limb.

According to the invention, effective amounts of autologous bone marrow are administered for treatment. As would be appreciated by experienced practitioners, the amount administered will depend upon many factors, including, but not limited to, the intended treatment, the severity of a condition being treated, the size and extent of an area to be treated, etc. With regard to treatment according to the invention, a representative protocol would be to administer quantities of from about 0.2 to about 0.5 ml of autologous bone marrow in each of from about 12 to about 25 injections, for a total of from about 2.4 to about 6 ml of autologous bone marrow being administered. Each dose administered could preferably comprise from about 1 to about 2 percent by volume of heparin or another blood anticoagulent, such as coumadin. When the autologous bone marrow has been cultured or stimulated and/or is being administered in combination with other pharmaceuticals or the like, the quantity of autologous bone marrow present should be approximately the same in each dose and/or the total of the autologous bone marrow administered should be about the same as described above. It is believed that the total number of cells of autologous bone marrow administered in each treatment should be on the order of from about $10^7$ to $5 \times 10^8$.

Optimization of angiogenic gene expression requires the co-administration of various angiogenic stimulants with the autologous bone marrow. Thus, according to the invention autologous bone marrow transplantation is injected either as a "stand alone" therapeutic agent or combined with any pharmacologic drug, protein or gene or any other compound or intervention that may enhance bone marrow production of angiogenic growth factors and/or promote endothelial cell proliferation, migration, and blood vessel tube formation. The "combined" agent(s) can be administered directly into the patient or target tissue, or incubated ex-vivo with bone marrow prior to injection of bone marrow into the patient. Examples of these "combined" agents (although not limited to these agents) are Granulocyte-Monocyte Colony Stimulatory Factor (GM-CSF), Monocyte Chemoattractant Protein 1 (MCP 1), EPAS1, or Hypoxia Inducible Factor-1 (HIF-1). The stimulation of the bone marrow could be by the direct exposure of the bone marrow to the factors in the form of proteins, or the bone marrow cells can be transfected with vectors carrying the relevant genes. For example, bone marrow can be transfected with a plasmid vector, or with an adenoviral vector, carrying the HIF-1 or EPAS1 transgenes. An example of an intervention that may enhance bone production of angiogenic factors is ex-vivo exposure of bone marrow cells to hypoxia. This intervention can be used alone with bone marrow, or in combination with any of the factors outlined above. These optimization strategies are designed to increase the production of vascular endothelial growth factor (VEGF) expression and/or other cytokines with angiogene activity prior to the direct injection of the bone marrow into the heart or any peripheral ischemic tissue. In a broad sense, the invention comprises intramyocardial injection of autologous bone marrow with any agent that would become available to cause stimulation of bone marrow and/or ex-vivo or in vivo stimulation of any angiogenic growth factor production by the bone marrow or its stromal microenvironment.

Delivery to patients will vary, dependent upon the clinical situation. For example, patients with refractory coronary artery disease or ischemic peripheral vasculopathy who will be candidates for a bone marrow aspiration procedure followed by autologous bone marrow myocardial or limb transplantation directed into the ischemic tissue or its borderline zone and/or normal tissue that may serve as the source for collateral or cellular supply to the diseased tissue for the purposes of therapeutic angiogensis and/or myogensis. For example, patients with refractory coronary artery disease or ischemic peripheral vasculopathy who will be candidates for a bone marrow aspiration procedure followed by autologous bone marrow myocardial or limb transplantation directed into the ischemic tissue or its bordeline zone and/or normal tissue that may serve as the source for collateral or cellular supply to the diseased tissue for the purposes of therapeutic angiogensis and/or myogensis. This procedure will involve the use of a bone marrow aspiration procedure, bone marrow harvesting and processing, followed by the use of the autologous bone marrow or its elements (growth factors and/or cellular elements being isolated from the patient's own bone marrow), with or without any ex-vivo stimulation of its delivery forms, to be injected into the ischemic or non ischemic myocardium and/or peripheral ischemic tissue (such as limb ischemia). The bone marrow will be kept in standard anti-coagulation/anti-aggregation solution (containing sodium citrate and EDTA) and kept in 4° C. in sterile medium until the time of its use.

Upon its use, the bone marrow will be filtered to avoid injecting remaining blood clots or macroaggregates into the target tissue.

The bone marrow, with or without a stimulatory agent in any of its delivery forms, or with or without having been transfected with a vector carrying a transgene that is designed to enhance the angiogenesis effect of the bone marrow, will be injected into the heart muscle, i.e., in therapeutic myocardial angiogenesis or therapeutic myogensis, using either any catheter-based trans-endocardial injection device or via a surgical (open chest) trans-epicardial thoracotomy approach, or any other approach that allows for transepicardial delivery. In the case of treatment of limb ischemia the bone marrow will be transferred by a direct injection of the bone marrow or it elements, with or without ex-vivo or in vivo stimulation in any of its delivery forms, into the muscles of the leg.

The volume of injection per treatment site will probably range between 0.1–5.0 cc per injection site, dependent upon the specific bone marrow product and severity of the ischemic condition and the site of injection. The total number of injections will probably range between 1–50 injection sites per treatment session.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A method of enhancing collateral blood vessel formation in a subject comprising directly administering to sites in heart or limb tissue an effective amount of autologous bone marrow aspirate to induce collateral blood vessel formation in the tissue.

2. The method of claim 1, wherein the autologous bone marrow aspirate is injected.

3. The method of claim 1, wherein the autologous bone marrow aspirate is injected intramyocardially.

4. The method of claim 2 wherein the wherein the autologous bone marrow aspirate is injected trans-epicardially or trans-endocardially.

5. The method of claim 4, wherein the trans-endocardial approach is via a catheter.

6. The method of claim 1, wherein the autologous bone marrow aspirate has been stimulated while growing in conditioned medium ex vivo, the conditioned medium comprising at least one agent selected from granulocyte-monocyte colony stimulating factor (GM-CSF), endothelial PAS domain 1 (EPAS1) and hypoxia inducible factor 1 (HIF-1).

7. The method of claim 6, wherein the autologous bone marrow aspirate has been stimulated by contact with one or more angiogenesis stimulating cytokines secreted therefrom while growing in conditioned medium ex vivo, the conditioned medium comprising at least one agent selected from granulocyte-monocyte colony stimulating factor (GM-CSF), endothelial PAS domain 1 (EPAS1) and hypoxia inducible factor 1 (HIF-1).

8. The method of claim 1, wherein the autologous bone marrow aspirate further comprises Monocyte Chemoattractant Protein 1 (MCP-1) or Vascular Endothelial Growth Factor (VEGF).

9. The method of claim 6, wherein the autologous bone marrow aspirate has been stimulated ex vivo in culture by transient exposure to hypoxia.

10. The method of claim 1, wherein the autologous bone marrow aspirate is administered in combination with one or more agent selected from a pharmacological drug or protein that enhances bone marrow production of angiogenic growth factors selected to promote endothelial cell proliferation, migration, or blood vessel formation.

11. The method of claim 10, wherein the autologous bone marrow aspirate and the agent or agents are administered together.

12. The method of claim 10, wherein the autologous bone marrow aspirate and the agent or agents are combined ex vivo prior to administration.

13. The method of claim 12, wherein the autologous bone marrow aspirate has been stimulated ex vivo in conditioned medium, the conditioned medium comprising at least one agent selected from granulocyte-monocyte colony stimulating factor (GM-CSF), endothelial PAS domain 1 (EPAS1) and hypoxia inducible factor 1 (HIF-1).

14. The method of claim 1, wherein the autologous bone marrow aspirate is administered to ischemic tissue.

15. The method of claim 12, further comprising culturing the autologous bone marrow aspirate to form conditioned medium containing bone marrow cells and endogenously secreted angiogenic cytokines and injecting the composition into ischemic heart tissue.

* * * * *